(12) United States Patent
Hiramoto et al.

(10) Patent No.: US 10,837,936 B2
(45) Date of Patent: Nov. 17, 2020

(54) ELECTROCHEMICAL MEASUREMENT SYSTEM, ELECTROCHEMICAL MEASUREMENT DEVICE, AND ELECTROCHEMICAL MEASUREMENT METHOD

(71) Applicant: Panasonic Intellectual Property Management Co., Ltd., Osaka (JP)

(72) Inventors: Kaoru Hiramoto, Osaka (JP); Masahiro Yasumi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 261 days.

(21) Appl. No.: 16/060,974

(22) PCT Filed: Mar. 6, 2017

(86) PCT No.: PCT/JP2017/008651
§ 371 (c)(1),
(2) Date: Jun. 11, 2018

(87) PCT Pub. No.: WO2017/154801
PCT Pub. Date: Sep. 14, 2017

(65) Prior Publication Data
US 2018/0364190 A1 Dec. 20, 2018

(30) Foreign Application Priority Data
Mar. 11, 2016 (JP) .................................. 2016-047705

(51) Int. Cl.
*G01N 27/27* (2006.01)
*G01N 33/483* (2006.01)
(Continued)

(52) U.S. Cl.
CPC ............... *G01N 27/27* (2013.01); *C12M 1/34* (2013.01); *G01N 27/301* (2013.01); *G01N 33/4836* (2013.01)

(58) Field of Classification Search
CPC .. G01N 27/27; G01N 33/4836; G01N 27/301; C12M 1/34
See application file for complete search history.

(56) References Cited

U.S. PATENT DOCUMENTS

| 7,208,077 B1 | 4/2007 | Albers et al. |
| 2005/0196776 A1 | 9/2005 | Yang |
| 2015/0260675 A1* | 9/2015 | Nakatani ................ C12M 41/36 204/403.01 |

FOREIGN PATENT DOCUMENTS

| WO | 2010/055942 | 5/2010 | |
| WO | WO-2014073195 A1 * | 5/2014 | ........... G01N 27/327 |

OTHER PUBLICATIONS

The Extended European Search Report dated Jun. 13, 2019 for the related European Patent Application No. 17763141.3.
(Continued)

*Primary Examiner* — J. Christopher Ball
(74) *Attorney, Agent, or Firm* — McDermott Will & Emery LLP

(57) ABSTRACT

An electrochemical measurement system includes an electrochemical measurement plate configured to have first and second biological samples placed thereon and an electrochemical measurement device connected to the electrochemical measurement plate. The electrochemical measurement plate includes a first well configured to have the first biological sample placed therein, a first measurement electrode group including first measurement electrodes provided within the first well, a second well configured to have the second biological sample placed therein, and a second measurement electrode group including second measure-
(Continued)

ment electrodes provided within the second well. The electrochemical measurement device includes measurement circuits, a switching section that connects the measurement circuits selectively to the first measurement electrode group and the second measurement electrode group, and a controller that controls a potential applied to the first measurement electrodes and a potential applied to the second measurement electrodes. This electrochemical measurement system has a small size.

4 Claims, 13 Drawing Sheets

(51) Int. Cl.
      *C12M 1/34*       (2006.01)
      *G01N 27/30*       (2006.01)

(56)       References Cited

OTHER PUBLICATIONS

International Search Report of PCT application No. PCT/JP2017/008651 dated Jun. 6, 2017.

\* cited by examiner

US 10,837,936 B2

ELECTROCHEMICAL MEASUREMENT SYSTEM, ELECTROCHEMICAL MEASUREMENT DEVICE, AND ELECTROCHEMICAL MEASUREMENT METHOD

This application is a U.S. national stage application of the PCT international application No. PCT/JP2017/008651 filed on Mar. 6, 2017, which claims the benefit of foreign priority of Japanese patent application No. 2016-047705 filed on Mar. 11, 2016, the contents all of which are incorporated herein by reference.

TECHNICAL FIELD

The present disclosure relates to an electrochemical measurement device and an electrochemical measurement method that are used for testing and analysis of biological samples including tissues and cells, such as embryos.

BACKGROUND ART

Biological samples, such as cells and tissues, such as fertilized embryos, transport various substances between their internal and external environments to perform activities. For example, an embryo inhales surrounding oxygen into cells by respiration, and undergoes cell division inside blastula while consuming the inhaled oxygen. Accordingly, development of the embryo can be inspected by measuring the amount of dissolved oxygen around the embryo. A method of electrically measuring a physiochemical status change that takes place around a living organism has been known as a procedure to measure the status of a biological sample.

A conventional measurement system for testing embryos includes a measurement plate and a measurement device. The measurement plate has plural wells therein. Each of the wells has an accommodation portion for accommodating an embryo, and plural electrodes provided around the accommodation portion. The measurement device is connected to the electrodes provided in the well. The measurement device electrochemically measures dissolved oxygen around the embryo with the electrodes.

PTL 1, for example, is known as prior art literature that relates to the present disclosure.

CITATION LIST

Patent Literature

PTL 1: International Publication WO2010/055942

SUMMARY

An electrochemical measurement system includes an electrochemical measurement plate configured to have first and second biological samples placed thereon and an electrochemical measurement device connected to the electrochemical measurement plate. The electrochemical measurement plate includes a first well configured to have the first biological sample placed therein, a first measurement electrode group including first measurement electrodes provided within the first well, a second well configured to have the second biological sample placed therein, and a second measurement electrode group including second measurement electrodes provided within the second well. The electrochemical measurement device includes measurement circuits, a switching section that connects the measurement circuits selectively to the first measurement electrode group and the second measurement electrode group, and a controller that controls a potential applied to the first measurement electrodes and a potential applied to the second measurement electrodes.

This electrochemical measurement system has a small size.

DETAILED DESCRIPTION OF PREFERRED EMBODIMENT

Figure 1:
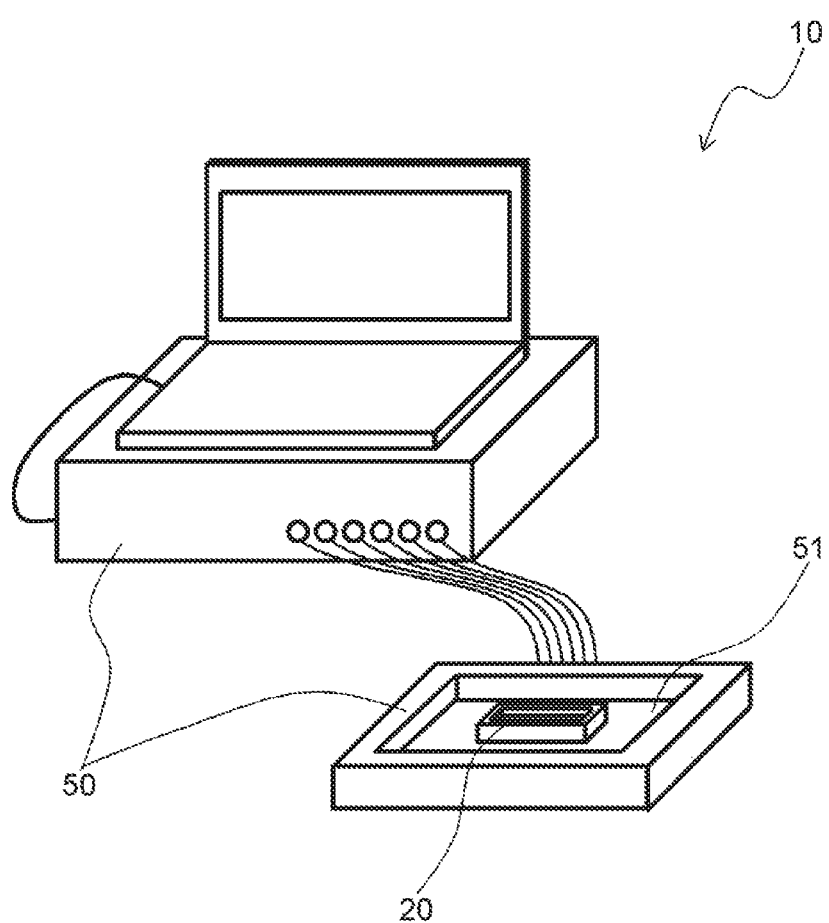
FIG. 1 is a schematic diagram of an electrochemical measurement system in accordance with an exemplary embodiment.

In a conventional measurement system, a measurement plate has wells therein. Each of the wells includes measurement electrodes. For that reason, the conventional measurement system requires the same number of measurement circuits as the measurement electrodes in order to carry out electrochemical measurement with all the measurement electrodes. However, such a measurement device equipped with the same number of measurement circuits as the measurement electrodes has a large size.

On the other hand, another conventional measurement system can carry out electrochemical measurement for measurement electrodes by switching over one measurement circuit to the measurement electrodes. When the measurement is carried out by the successive switching over of one measurement circuit, it takes a long time to complete the measurement for all the measurement electrodes.

An electrochemical measurement systems and an electrochemical measurement method in accordance with an exemplary embodiment of the present disclosure will be detailed below with reference to drawings. The exemplary embodiment described below illustrates specific examples of the present disclosure. Accordingly, the numerical values, shapes, materials, structural elements, arrangements and connections of structural elements, etc. shown in the following exemplary embodiment are merely examples, and therefore, do not limit the scope of the present disclosure. Therefore, among the constituent elements in accordance with the embodiment, those not recited in any one of the independent claims which indicate the broadest inventive concepts of the present invention are described as optional elements.

The drawings are schematic and do not necessarily depict the elements exactly. In the drawings, substantially the same parts are designated by the same reference numerals, and the repetitive description thereof may be omitted or simplified.

FIG. 1 is a schematic view of electrochemical measurement system 100 according to an exemplary embodiment. Electrochemical measurement system 100 performs electrochemical measurement of biological samples. Electrochemical measurement system 10 includes electrochemical measurement plate 20 and electrochemical measurement device 50. Electrochemical measurement system 10 is used for, for example, measurement of a mass of biological sample. A mass of biological sample may be, for example, a cell mass, such as an embryo. The cell mass may be either a single cell or an aggregate of plural cells. The term "embryo" includes a fertilized egg that has not yet divided.

Figure 2:
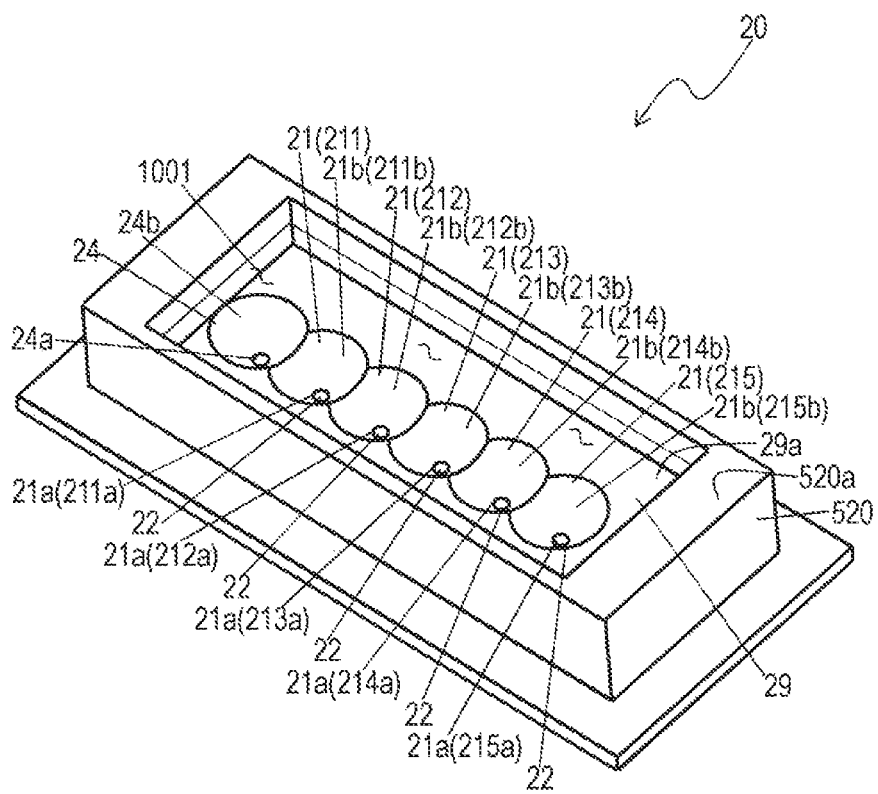
FIG. 2 is a perspective view of an electrochemical measurement plate of the electrochemical measurement system in accordance with the embodiment.

FIG. 2 is a schematic perspective view of electrochemical measurement plate 20. Electrochemical measurement plate 20 includes reservoir 29 having a liquid, such as a measurement solution and a culture medium, placed therein, and plural wells 21 and 24 provided in bottom surface 29a of reservoir 29. Specifically, electrochemical measurement plate 20 includes substrate 520. Reservoir 29 is provided on upper surface 520a of substrate 520. Reservoir 29 accommodates plural biological samples 102 (1021 to 1025) and measurement solution 1001 which has electrical conductivity.

Measurement solution 1001 fills reservoir 29 and wells 21 while biological samples 1021 to 1025 are placed in wells 211 to 215, respectively. Electrochemical measurement plate 20 includes wells 21 configured to have biological samples 102 placed thereon, thereby allowing electrochemical measurement plate 20 to measure biological samples 102 at once.

Electrochemical measurement plate 20 shown in FIG. 2 includes five wells 21 (211, 212, 213, 214, 215) configured to have biological samples placed therein. Electrochemical measurement plate 20 further includes well 24 configured not to have a biological sample placed therein. Electrochemical measurement plate 20 further includes well 24 configured not to have a biological sample placed therein. Wells 24 and 21 (211, 212, 213, 214, and 215) have bottom surfaces 24a and 21a (211a, 212a, 213a, 214a, and 215a), and side wall surfaces 24b and 21b (211b, 212b, 213b, 214b, and 215b). Side wall surfaces 24b and 21b (211b, 212b, 213b, 214b, and 215b) are connected to bottom surfaces 24a and 21a (211a, 212a, 213a, 214a, and 215a) and bottom surface 29a of reservoir 29.

Figure 3A:
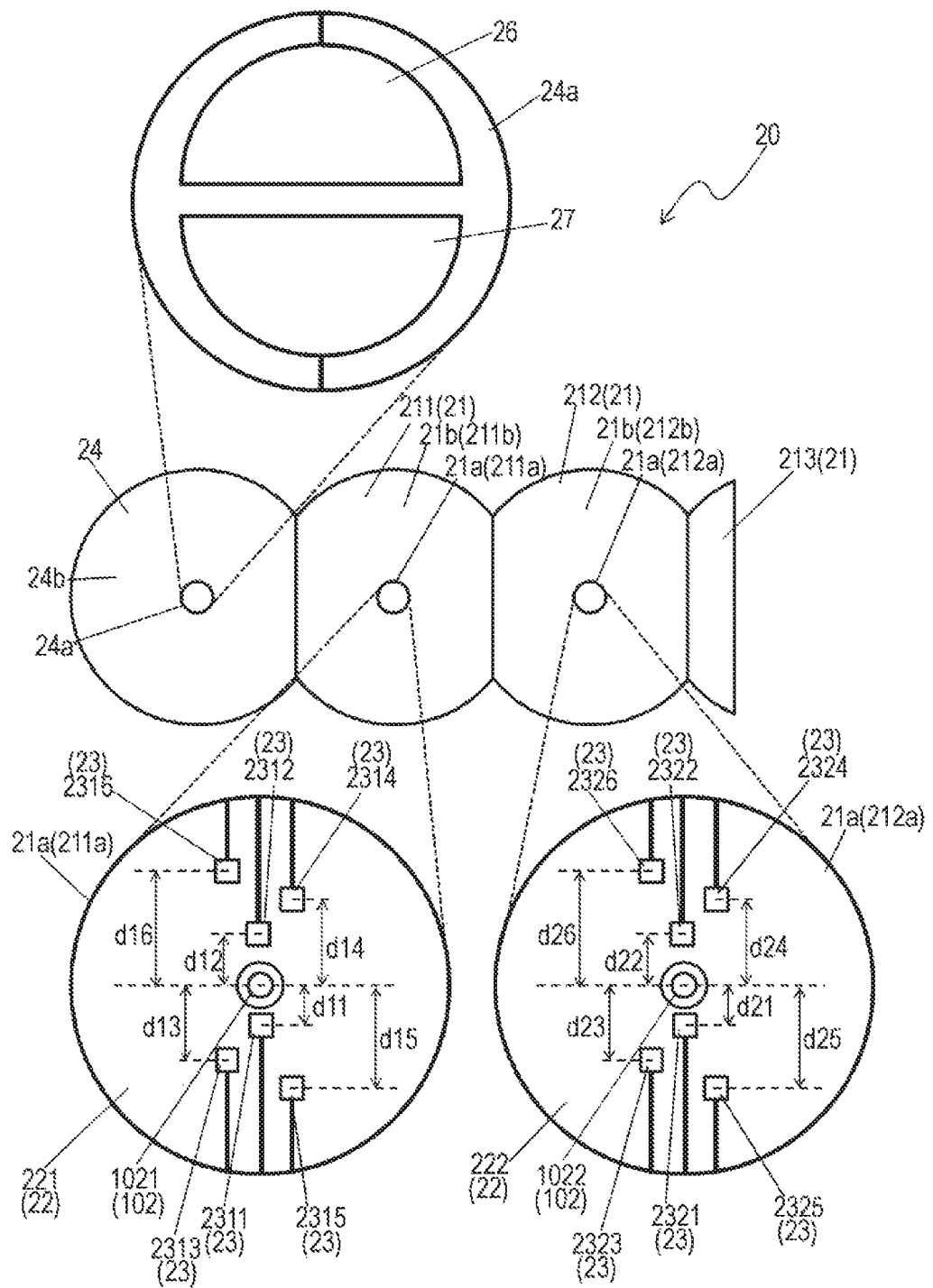
FIG. 3A is a top view of the electrochemical measurement plate in accordance with the embodiment.

FIG. 3A is a top view of electrochemical measurement plate 20 for illustrating wells 21 and 24 enlarged. Well 211 includes mount portion 221 provided at a central portion of the bottom surface of well 211. Mount portion 221 is configured to have a biological sample placed thereon. Similarly, well 212 includes mount portion 222 provided at a central portion of the bottom surface of well 212. Mount portion 222 is configured to have a biological sample placed thereon. Thus, each of plural wells 21 includes mount portion 22 configured to have a biological sample placed thereon. Mount portion 22 may be a recessed portion or a mark that indicates a mount location, which is provided in the bottom surface of each of wells 21.

Electrochemical measurement plate 20 includes plural measurement electrodes 23 each provided around mount portion 22 of respective one of wells 21.

For example, well 211 includes six measurement electrodes 2311, 2312, 2313, 2314, 2315, and 2316 provided within well 211 around mount portion 221 in well 211. Mount portion 221 is apart from measurement electrodes 2311, 2312, 2313, 2314, 2315, and 2316 by distances $d11$, $d12$, $d13$, $d14$, $d15$, and $d16$, respectively. Distance $d11$ between mount portion 221 and measurement electrode 2311 is less than distance $d12$ between mount portion 221 and measurement electrode 2312. Distance $d12$ is less than distance $d13$ between mount portion 221 and measurement electrode 2313. Distance $d13$ is less than distance $d14$ between mount portion 221 and measurement electrode 2314. Distance $d14$ is less than distance $d15$ between mount portion 221 and measurement electrode 2315. Distance $d15$ is less than distance $d16$ between mount portion 221 and measurement electrode 2316.

Similarly to well 211, well 212 has six measurement electrodes 2321, 2322, 2323, 2324, 2325, and 2326 provided within well 212 around mount portion 222. Mount portion 222 is apart from measurement electrodes 2321, 2322, 2323, 2324, 2325, and 2326 by distances $d21$, $d22$, $d23$, $d24$, $d25$, and $d26$, respectively. Distance $d21$ between mount portion 222 and measurement electrode 2321 is less than distance $d22$ between mount portion 222 and measurement electrode 2322. Distance $d22$ is less than distance $d23$ between mount portion 222 and measurement electrode 2323. Distance $d23$ is less than distance $d24$ between mount portion 222 and measurement electrode 2324. Distance $d24$ is less than distance $d25$ between mount portion 222 and measurement electrode 2325. Distance $d25$ is less than distance $d26$ between mount portion 222 and measurement electrode 2326.

Measurement electrodes 23 provided in each well 21 constitute a measurement electrode group. Measurement electrodes 2311, 2312, 2313, 2314, 2315, and 2316 provided within well 211 around mount portion 221 constitute measurement electrode group 231. Measurement electrodes 2321, 2322, 2323, 2324, 2325, and 2326, provided within well 212 around mount portion 222 constitute measurement electrode group 232.

Thus, in each well 21, plural measurement electrodes 23 are disposed at positions apart from mount portion 22 by different distances. Measurement electrodes 23 apart from mount portion 22 by different distances allows electrochemical measurement plate 20 to measure current values corresponding to the distances from the biological samples.

Distance $d11$ in well 211 is equal to distance $d21$ in well 212. Distance $d12$ in well 211 is equal to distance $d22$ in well 212. Distance $d13$ in well 211 is equal to distance $d23$ in well 212. Distance $d14$ in well 211 is equal to distance $d24$ in well 212. Distance $d15$ in well 211 is equal to distance $d25$ in well 212. Distance $d16$ in well 211 is equal to distance $d26$ in well 212.

Each of measurement electrodes 23 in well 211 is thus provided at a position at a distance equal to the distance between mount portion 22 and respective one of measurement electrodes 23 provided in well 212. In each well 21, measurement electrodes 23 have the same positional relationship as described above.

Well 24 includes counter electrode 2 provided in well 24 and reference electrode 27 provided in well 24. Well 24 does not necessarily include mount portion 22 and measurement electrodes 23.

Figure 3B:
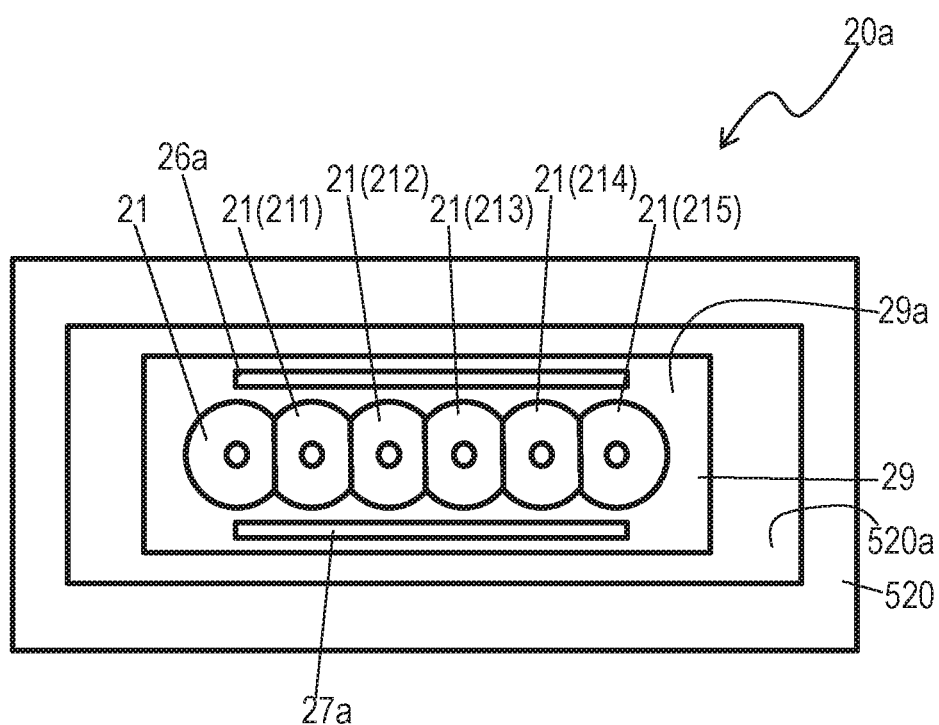
FIG. 3B is a top view of another electrochemical measurement plate in accordance with the embodiment.

FIG. 3B is a top view of another electrochemical measurement plate 20a in accordance with the embodiment. In FIG. 3B, components identical to those of electrochemical measurement plate 20 shown in FIG. 3A are denoted by the same reference numerals. Electrochemical measurement plate 20a includes counter electrode 26a and reference electrode 27a disposed on bottom surface 29a of reservoir 29 outside wells 21 and 24 instead of counter electrode 26 and reference electrode 27 of electrochemical measurement plate 20 shown in FIG. 3A. Electrochemical measurement plate 20a includes wells 21 each including plural measurement electrodes 23 instead of well 24 including counter electrode 26 and reference electrode 27 of electrochemical measurement plate 20 shown in FIG. 3A. While a measurement solution is accommodated in reservoir 29, counter electrode 26a and reference electrode 27a contrast the measurement solution.

Figure 4:
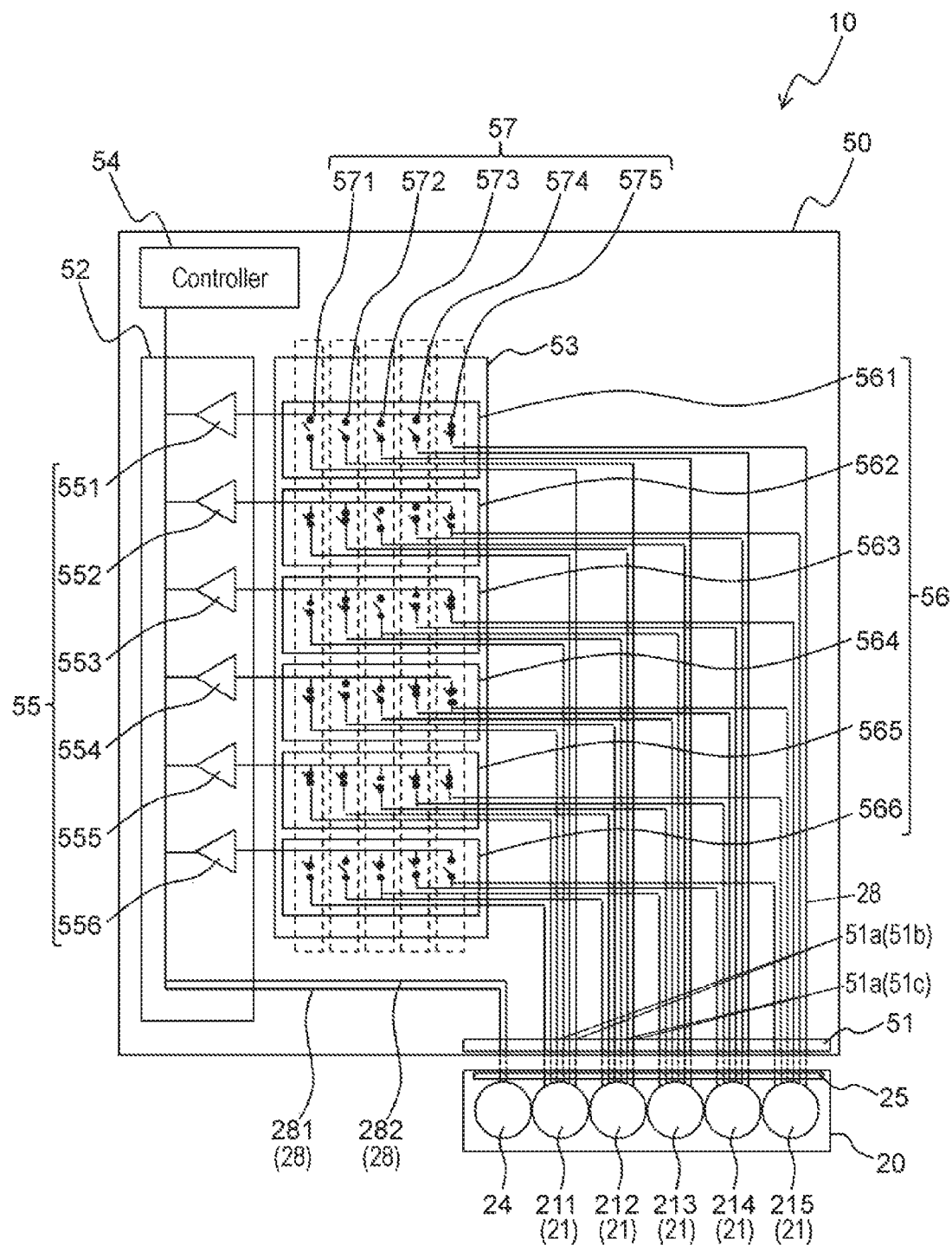
FIG. 4 is a circuit diagram of an electrochemical measurement device in accordance with the embodiment.

FIG. 4 is a circuit diagram of electrochemical measurement device 50.

Electrochemical measurement device 50 includes connector 51, measurement unit 52, switching section 53, and controller 54.

Electrochemical measurement plate 20 is placed on connector 51. Electrochemical measurement plate 20 includes outlet electrode portion 25 connected to measurement electrode 23, counter electrode 26, and reference electrode 27 via wirings 28. Connector 51 includes connector terminals 51a connected to measurement electrodes 23, counter electrode 26, and reference electrode 27 via outlet electrode portion 25 of electrochemical measurement plate 20.

Measurement unit 52 includes plural measurement circuits 55. Specifically, measurement unit 52 includes the same number of measurement circuits 55 as measurement electrodes 23 provided per one well 21 of electrochemical measurement plate 20. For example, when an N number of measurement electrodes are provided around mount portion 22 in one well 21, electrochemical measurement device 50 includes an N number of measurement circuits 55, where N is an integer greater than or equal to two. In electrochemical measurement plate 10 shown in FIG. 4, N is six, and measurement unit 52 includes six measurement circuits 55 (551, 552, 553, 554, 555, and 556), accordingly.

Each of measurement circuits 55 may be implemented by, for example, an operational amplifier that measures a current value. Measurement circuit 55 measures values of the current flowing between measurement electrodes 23 and counter electrode 26.

Switching section 53 switches measurement electrodes 23 to be connected to measurement circuits 55 from one to another. Switching section 53 includes the same number of switching units 56 as measurement circuits 55 of electrochemical measurement device 50. For example, in the case that electrochemical measurement device 50 includes an N number of measurement circuits 55, switching section 53 includes an N number of switching units 56. In FIG. 4, switching section 53 includes six switching units (561, 562, 563, 564, 565, and 566).

Each switching unit 56 includes plural switching elements 57. Each switching unit 56 includes the same number of switching elements 57 as wells 21 used for measurement of samples in electrochemical measurement plate 20.

For example, in the case that electrochemical measurement plate 20 includes an M number of wells 21 configured to have samples placed therein, each switching unit 56 includes an M number of switching elements 57. In electrochemical measurement system shown in FIG. 4, the number M is five. For example, switching unit 561 includes five switching elements 571, 572, 573, 574, and 575.

Switching element 57 may be implemented by either a mechanical switch or an electromagnetic switch.

Each of measurement circuits 55 is connected to respective one of switching units 56. Each of switching elements 57 provided in one of switching units 56 are connected to respective one of plural measurement electrodes 23 provided in electrochemical measurement plate 20 via connector 51 and outlet electrode portion 25. Plural switching elements 57 within one of switching units 56 are connected to respective one of measurement electrodes 23 provided in respective one of different well 21 of electrochemical measurement plate 20.

For example, switching unit 561 is connected to measurement circuit 551. In switching unit 561, switching element 571 is connected to measurement electrode 2311 in well 211. Switching element 572 is connected to measurement electrode 2321 in well 212. Similarly, switching elements 573, 574, and 575 are connected to measurement electrodes 23 of wells 213, 214, 215, respectively.

Thus, measurement electrodes 23 provided in a certain one of wells 21 are not connected to plural switching elements 57 within one of switching units 56. In switching section 53 shown in FIG. 4, six switching elements among plural switching elements 57 that are surrounded by a box of dashed lines are connected to measurement electrodes 2311, 2312, 2313, 2314, 2315, and 2316 all of which are provided within the same well 21. Controller 54 controls switching section 53 such that six switching elements 57 surrounded by each box of dashed lines shown in FIG. 4 are turned on and off simultaneously to one another. Switching section 53 designates switching elements 57 surrounded by a box of dashed lines as one group, and turns on and off the switching elements, group by group.

The above configuration allows the electrochemical measurement to perform measurement while successively switching wells 21 one after another by switching of switching units 56 with measurement electrodes 23 of electrochemical measurement plate 20. In addition, switching section 53 simultaneously turns on and off switching elements 57 in plural switching units 56. At this moment, switching section 53 switches switching elements 57 such that measurement electrodes 23 of electrochemical measurement plate 20 measured by each measurement circuit 55 of measurement circuits 55 are measurement electrodes 23 provided in one well. This configuration allows electrochemical measurement device 50 to measure measurement electrodes 23 provided within one well 21 simultaneously. By controlling switching section 53, electrochemical measurement device 50 can perform the measurement while switching measurement electrodes 23 to be measured by measurement circuits 55 simultaneously for each well 21.

In the electrochemical measurement of a biological sample, the measured current value may gradually decrease when a potential is applied to measurement electrode 23 to flow a current through measurement electrode 23. Consequently, when current values flowing through different measurement electrodes 23 are measured at different timings in one of wells 21, the current value that serves as the reference may change, hence hardly performing analysis of the measured values. Moreover, when fluctuated current values are used, the accuracy of the measurement may degrade.

Electrochemical measurement system 10 in accordance with the embodiment of the present disclosure can carry out electrochemical measurement within the same well 21 at the same timing. This configuration allows the current values to be analyzed easily, and improves the accuracy of the electrochemical measurement. Furthermore, since current values are measured while switching over measurement circuits 55 for each of the wells 21, the number of measurement circuits 55 can be reduced, accordingly reducing the size of electrochemical measurement device 50 accordingly.

In electrochemical measurement system 10, counter electrode 26 and reference electrode 27 are connected to controller 54. Wiring 281 between counter electrode 26 and controller 54 and wiring 282 between reference electrode 27 and controller 54 are not connected to switching section 53. For this reason, counter electrode 26 and reference electrode 27 are not changed in the measurement. Counter electrode 26 and reference electrode 27 are commonly used in measurement for each of wells 21.

One of switching units 56 is preferably connected to measurement electrodes 23 that are located at an equal distance from mount portions 22 of respective wells 21.

For example, switching unit 561 is connected to measurement electrode 2311 of well 211 and measurement electrode 2321 of well 212. In each of wells 213 to 215, each of measurement electrodes 23 disposed at a position that is spaced apart by distance d1 from respective one of mount portions 22 is connected to switching unit 561.

Similarly, as for the other switching units 562 to 566 as well, each of measurement electrodes 23 that are spaced apart by an equal distance from respective one of mount portions 22 in wells 21 are connected to respective one of switching units 56.

This configuration can perform the electrochemical measurement for each of measurement electrodes 23 that are spaced apart by an equal distance from biological samples with respective one of measurement circuits 55. This configuration reduces variations in the measurement between different measurement circuits 55. As a result, it is possible to accurately measure a change in current value originating from the biological sample.

Controller 54 controls switching operations of switching elements 57 of switching section 53, the level of the potential applied between measurement electrodes 23 and counter electrode 26, and the timing at which the potential is applied. Measurement circuits 55 measure the current values flowing through measurement circuits 55 due to a potential applied between counter electrode 26 and each of measurement electrodes 23. Since controller 54 controls switching of switching elements 57, measurement circuits 55 may be connected to specific measurement electrodes 23. As a result, measurement circuits 55 can measure values of the current flowing through specific measurement electrodes 23.

Figure 5:
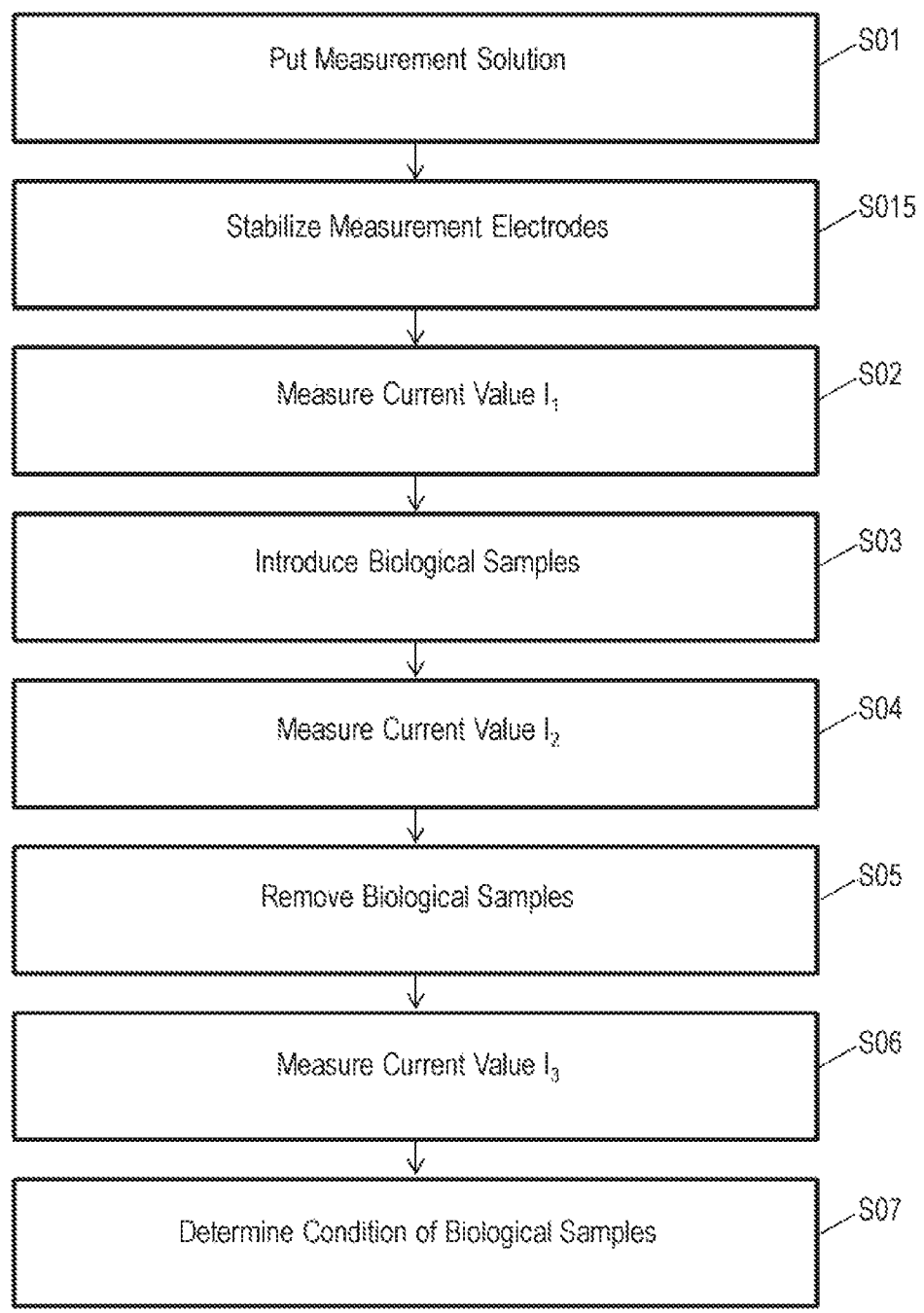
FIG. 5 is a flowchart illustrating an electrochemical measurement method in accordance with the embodiment.
Figure 6:
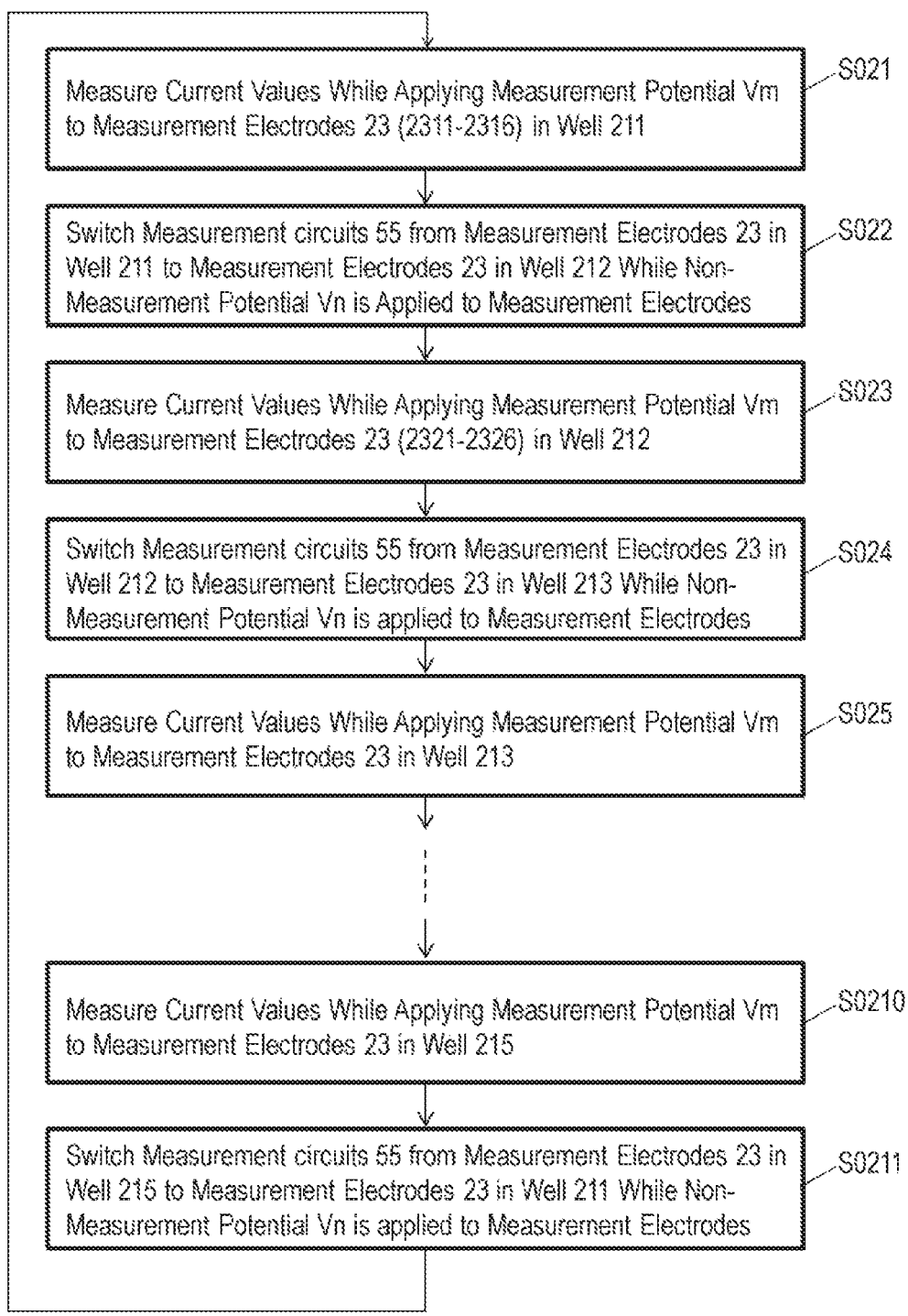
FIG. 6 is a flowchart illustrating the electrochemical measurement method in accordance with the embodiment.

An electrochemical measurement method in electrochemical measurement system 10 will be described below. FIGS. 5 and 6 are flowcharts illustrating the electrochemical measurement method.

Electrochemical measurement plate 20 is placed on electrochemical measurement device 50 as shown in FIG. 1. After that, measurement solution 1001 is put in wells 21 of electrochemical measurement plate 20 such that measurement solution 1001 contacts measurement electrodes 23, counter electrode 26, and reference electrode 27 (step S01).

Next, measurement electrodes 23 are stabilized (step S015). Specifically, a predetermined potential V is applied to measurement electrodes 23 in each of wells 21. The predetermined potential V may be, for example, measurement potential Vm at the time of measurement for a biological sample.

After that, in each of wells 21, measurement potential Vm is applied between counter electrode 26 and each of measurement electrodes 23 to measure current value $I_1$ flowing through measurement electrode 23 (step S02). While switching section 53 switches measurement electrodes 23 that are connected to measurement circuits 55 from one well 21 to another well 21, measurement circuits 55 measure current value $I_1$ of measurement electrodes 23 in well 211 to well 215 sequentially, one by one.

Figure 7:
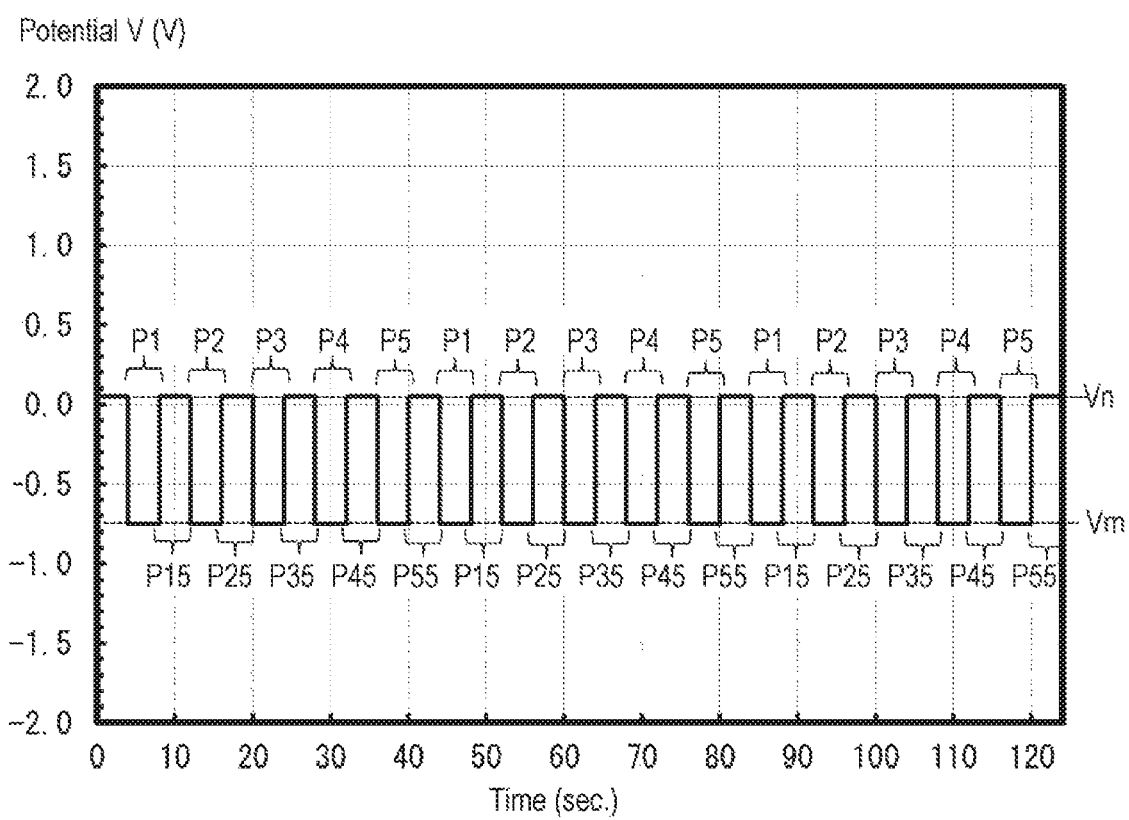
FIG. 7 is a graph illustrating a voltage during an operation of the electrochemical measurement system in accordance with the embodiment.

FIG. 6 shows the operations of switching section 53 when measurement circuits 55 measure current values $I_1$ in plural wells 21 in step S02. FIG. 7 shows potential V applied to measurement electrodes 23 in the operation of electrochemical measurement system 10. In FIG. 7, the vertical axis represents potential V applied to measurement electrodes 23, and the horizontal axis represents time.

As illustrated in FIG. 7, in electrochemical measurement system 10, electrochemical measurement device 50 applies measurement potential Vm and non-measurement potential Vn alternately to measurement electrodes 23 at constant intervals. Thus, potential V applied to measurement electrodes 23 has a pulse waveform alternately repeating measurement potential Vm and non-measurement potential Vn at the constant intervals. Measurement potential Vm is a potential that is applied when measuring a value of current flowing through measurement electrodes 23 of electrochemical measurement for a biological sample. Non-measurement potential Vn is determined such that no electric current flows through measurement electrodes 23 under the condition in which electrochemical measurement plate 20 is connected to electrochemical measurement device 50.

In period P1, measurement circuits 55 are connected to an N number of measurement electrodes 23 in well 211 via switching section 53. Controller 54 applies measurement potential Vm to the N number of measurement electrodes 23 of well 211. Measurement circuits 55 measure respective current values $I_1$ flowing through the N number of measurement electrodes 23 in well 211 (step S021).

In period P15 subsequent to period P1, controller 54 applies non-measurement potential Vn to the N number of measurement electrodes 23 in well 211. While non-measurement potential Vn is applied to the N number of measurement electrodes 23 of well 211, switching section 53 switches measurement electrodes 23 that are connected to measurement circuits 55 from measurement electrodes 23 of well 211 to measurement electrodes 23 of well 212 (step S022). That is, while non-measurement potential Vn is applied to the N number of measurement electrodes 23 of well 211, switching section 53 disconnects measurement circuits 55 from measurement electrodes 23 of well 211 and connects measurement circuits 55 to measurement electrodes 23 of well 212.

In period P2 subsequent to period P15, controller 54 applies measurement potential Vm to measurement electrodes 23 of well 213. Measurement circuits 55 measure respective current values $I_1$ flowing through measurement electrodes 23 of well 213 (step S023).

In period P25 subsequent to period P2, controller 54 applies non-measurement potential Vn to the N number of measurement electrodes 23 of well 212. While non-measurement potential Vn is applied to the N number of measurement electrodes 23 of well 212, switching section 53 switches measurement electrodes 23 that are connected to measurement circuits 55 from measurement electrodes 23 of well 212 to measurement electrodes 23 of well 213. That is, while non-measurement potential Vn is applied to the N number of measurement electrodes 23 of well 212, switching section 53 disconnects measurement circuits 55 from measurement electrodes 23 of well 212 and connects measurement circuits 55 to measurement electrodes 23 of well 213 (step S024).

In period P3 subsequent to period P25, controller 54 applies measurement potential Vm to measurement electrodes 23 of well 213. Measurement circuits 55 measure respective current values $I_1$ flowing through measurement electrodes 23 of well 213 (step S025).

In period P35 subsequent to period P3, controller 54 applies non-measurement potential Vn to the N number of measurement electrodes 23 of well 213. While non-measurement potential Vn is applied to the N number of measurement electrodes 23 of well 213, switching section 53 switches measurement electrodes 23 that are connected to measurement circuits 55 from measurement electrodes 23 of well 213 to measurement electrodes 23 of well 214. That is, while non-measurement potential Vn is applied to the N number of measurement electrodes 23 of well 213, switching section 53 disconnects measurement circuits 55 from measurement electrodes 23 of well 213 and connects measurement circuits 55 to measurement electrodes 23 of well 214.

In period P4 subsequent to period P35, controller 54 applies measurement potential Vm to measurement electrodes 23 of well 214. Measurement circuits 55 measure respective current values $I_1$ flowing through measurement electrodes 23 of well 214.

In period P45 subsequent to period P4, controller 54 applies non-measurement potential Vn to the N number of measurement electrodes 23 of well 214. While non-measurement potential Vn is applied to the N number of measurement electrodes 23 of well 214, switching section 53 switches measurement electrodes 23 that are connected to measurement circuits 55 from measurement electrodes 23 of well 214 to measurement electrodes 23 of well 215. That is, while non-measurement potential Vn is applied to the N number of measurement electrodes 23 of well 214, switching section 53 disconnects measurement circuits 55 from measurement electrodes 23 of well 214 and connects measurement circuits 55 to measurement electrodes 23 of well 215.

In period P5 subsequent to period P45, controller 54 applies measurement potential Vm to measurement electrodes 23 of well 215. Measurement circuits 55 measure respective current values $I_1$ flowing through measurement electrodes 23 of well 215 (step S0210).

Electrochemical measurement device 50 thus measures current values $I_1$ flowing through measurement electrodes 23 of each well while successively switching wells from well 211 to well 215.

In accordance with the embodiments, period P55 subsequent to period P5, controller 54 applies non-measurement potential Vn to the N number of measurement electrodes 23 of well 215. While non-measurement potential Vn is applied to the N number of measurement electrodes 23 of well 215, switching section 53 switches measurement electrodes 23 that are connected to measurement circuits 55 from measurement electrodes 23 of well 215 to measurement electrodes 23 of well 211 (step S0211). That is, while non-measurement potential Vn is applied to the N number of measurement electrodes 23 of well 215, switching section 53 disconnects measurement circuits 55 from measurement electrodes 23 of well 215 and connects measurement circuits 55 to measurement electrodes 23 of well 211.

In period P1 subsequent to period P55, controller 54 applies measurement potential Vm to measurement electrodes 23 of well 211. Measurement circuits 55 measure respective current values $I_1$ flowing through measurement electrodes 23 of well 211 (step S021). As illustrated in FIG. 7, controller 54 repetitively performs measurement of current values $I_1$ in periods P1 to P5 plural times.

As described above, when current values $I_1$ is measured, switching elements 57 of switching units 56 are switched while non-measurement potential Vn is applied. This configuration reduces current noise generated due to the switching of switching elements 57, thereby measuring current values $I_1$ accurately.

Figure 8:
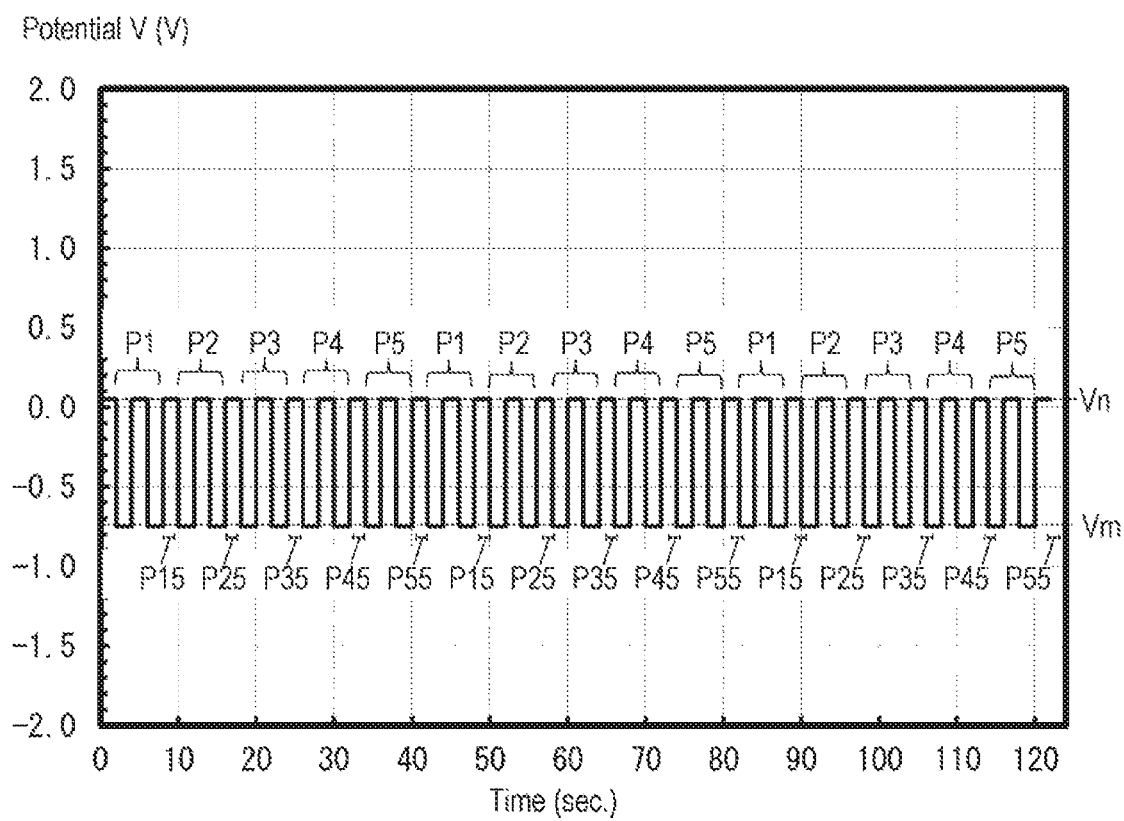
FIG. 8 is a graph illustrating a voltage during another operation of the electrochemical measurement system in accordance with the embodiment.

FIG. 8 shows potential V applied to measurement electrodes 23 in another operation of electrochemical measurement system 10. In FIG. 8, the vertical axis represents potential V applied to measurement electrodes 23, and the horizontal axis represents time. In the operation shown in FIG. 7, controller 54 applies, to measurement electrodes 23, potential V having a pulse waveform alternately repeating measurement potential Vm and non-measurement potential Vn at constant intervals in periods P1 to P5. In this case, during the time in which measurement is performed for a certain one of wells 21, switching section 53 does not perform the switching operation even when non-measurement potential Vn is applied. Then, at the timing when non-measurement potential Vn is applied after the measurement for one of wells 21 has been completed, switching section 53 carries out the switching operation.

Subsequently, as illustrated in FIG. 5, one biological sample is introduced to be placed on mount portion 22 of each one of wells 21 in electrochemical measurement plate 20 (step S03). The biological sample is placed while measurement potential Vm is not applied. More preferably, the biological sample may be placed while a potential at which no current flows through electrochemical measurement device 50 is applied, in other words, while non-measurement potential Vn is applied.

While the biological sample is placed, measurement potential Vm is applied to measurement electrodes 23 in each of wells 21 to measure current values $I_2$ flowing through measurement electrodes 23 (step S04). In step S04, similarly to the measurement of current value $I_1$ in step S02 (steps S021 to S0210), measurement circuits 55 successively measure current values $I_2$ flowing through measurement electrodes 23 in wells 211 to 215 sequentially while measurement electrodes 23 connected to measurement circuits 55 in each one of wells 21 are switched by switching section 53.

After measuring current values $I_2$ in step S04, the biological samples are removed from wells 21 (step S05). When removing the biological samples, it is preferable that measurement potential Vm not be applied. More preferably, the biological samples may be removed while non-measurement potential Vn is applied.

After removing the biological samples from wells 21 in step S05, similarly to step S02 (steps S021 to S0210), measurement potential Vm is applied to measurement electrodes 23 in each of wells 21 to measure current values $I_3$ flowing through measurement electrodes 23 (step S06). Similarly to the measurement of current value $I_1$, measurement circuits 55 successively measure current values $I_3$ for well 211 to well 215, one by one, while switching section 53 changes measurement electrodes 23 connected to measurement circuits 55 for one of wells 21 to another of wells 21.

The condition of each of the biological samples is determined based on current values $I_1$, $I_2$, and $I_3$ (step S07). For example, when the condition of an embryo is investigated, the concentration of dissolved oxygen around the embryo is calculated based on current values $I_1$, $I_2$, and $I_3$. By obtaining the concentration of dissolved oxygen around the embryo, it is possible to investigate the activity of the embryo.

In electrochemical measurement of biological samples, the measured current value may change over time. Consequently, when the measurement is conducted for one biological sample by switching plural measurement electrodes, it is difficult to accurately measure the condition of the biological sample since the reference current value may change depending on the timing of the measurement. For this reason, it is preferable that the measurement of one biological sample with plural measurement electrodes is carried out at the same timing. It is possible to measure an accurate condition of a biological sample by measuring current values at the same timing, as with electrochemical measurement system 10 in accordance with the embodiment.

When not all the wells 21 are used in the measurement, that is, when wells 21 may include a well having no biological sample placed therein, switching section 53 may switch connection between measurement circuits 55 and measurement electrodes 23 for only wells out of wells 21 having the biological samples placed therein and used for the measurement. Specifically, for example, when the biological samples are introduced into three wells 211, 213, and 215 of electrochemical measurement plate 20, switching unit 561 of switching section 53 turns on and off switching elements 571, 573, and 575, and continuously turns off switching elements 572 and 574. Switching units 562 to 566 also control the corresponding switching elements similarly to that used by switching unit 561.

The electrochemical measurement method in accordance with the present disclosure allows currents flowing through measurement electrodes 23 provided within the same one of wells 21 to be measured simultaneously by the same number of measurement circuits 55 as measurement electrodes 23 provided within each well 21. Therefore, it is possible to conduct electrochemical measurement of biological samples accurately.

As described above, electrochemical measurement system 10 includes electrochemical measurement plate 20 configured to have biological samples 1021 and 1022 placed thereon and electrochemical measurement device 50 connected to electrochemical measurement plate 20. Electrochemical measurement plate 20 includes wells 211 and 212, measurement electrode group 231 provided within well 211, and measurement electrode group 232 provided within well 212. Well 211 includes mount portion 221 configured to have biological sample 1021 placed thereon. Measurement electrode group 231 includes an N number of measurement electrodes 23 provided around mount portion 221, where N is an integer greater than or equal to two. Well 212 includes mount portion 222 configured to have biological sample 1022 placed thereon. Measurement electrode group 232 includes an N number of measurement electrodes 23 provided around mount portion 222. Electrochemical measurement device 50 includes an N number of measurement circuits 55, switching section 53 connected to the N number of measurement circuits 55 and measurement electrode groups 231 and 232, and controller 54 that controls a potential applied to measurement electrodes 23. Switching section 53 connects the N number of measurement circuits 55 selectively to measurement electrode group 231 and measurement electrode group 232.

Distance d11 between mount portion 221 and certain measurement electrode 2311 out of the N number of measurement electrodes 23 may be less than distance d12 between mount portion 221 and further measurement electrode 2312 out of the N number of measurement electrodes 23. Distance d21 between mount portion 222 and certain measurement electrode 2321 out of the N number of measurement electrodes 23 may be less than distance d22 between mount portion 222 and further measurement electrode 2322 out of the N number of measurement electrodes 23. Distance d11 may be equal to distance d21. Distance d12 may be equal to distance d22. Switching section 53 includes switching units 561 and 562. Switching unit 561 connects measurement circuit 551 selectively to certain measurement electrode 2311 and certain measurement electrode 2321. Switching section 562 connects measurement circuit 552 out of the N number of measurement circuits 55 selectively to further measurement electrode 2312 and further measurement electrode 2322.

Electrochemical measurement plate 20 may further include counter electrode 26. In this case, electrochemical measurement device 50 may further include wiring 281 that is connected between counter electrode 26 and controller 54 but is not connected to switching section 53.

Electrochemical measurement device 50 includes electrode group 51b including an N number of connector terminals 51a, where N is an integer greater than or equal to two, electrode group 51c including an N number of connector terminals 51a, an N number of measurement circuits 55, switching section 53 that connects the N number of measurement circuits 55 selectively to electrode group 51b and electrode group 51c, and controller 54. The N number of connector terminals 51a are configured to be connected to the N number of measurement electrodes 23 of electrochemical measurement plate 20, respectively. The N number of connector terminals 51a are configured to be connected to the N number of measurement electrodes 23 of electrochemical measurement plate 20, respectively.

Electrochemical measurement device 50 may further include wirings 281 that connects controller to connector terminals 51a but is not connected with switching section 53.

Modification 1

Modification 1 of the electrochemical measurement device according to the embodiment will be described below with reference to drawings.

Figure 9A:
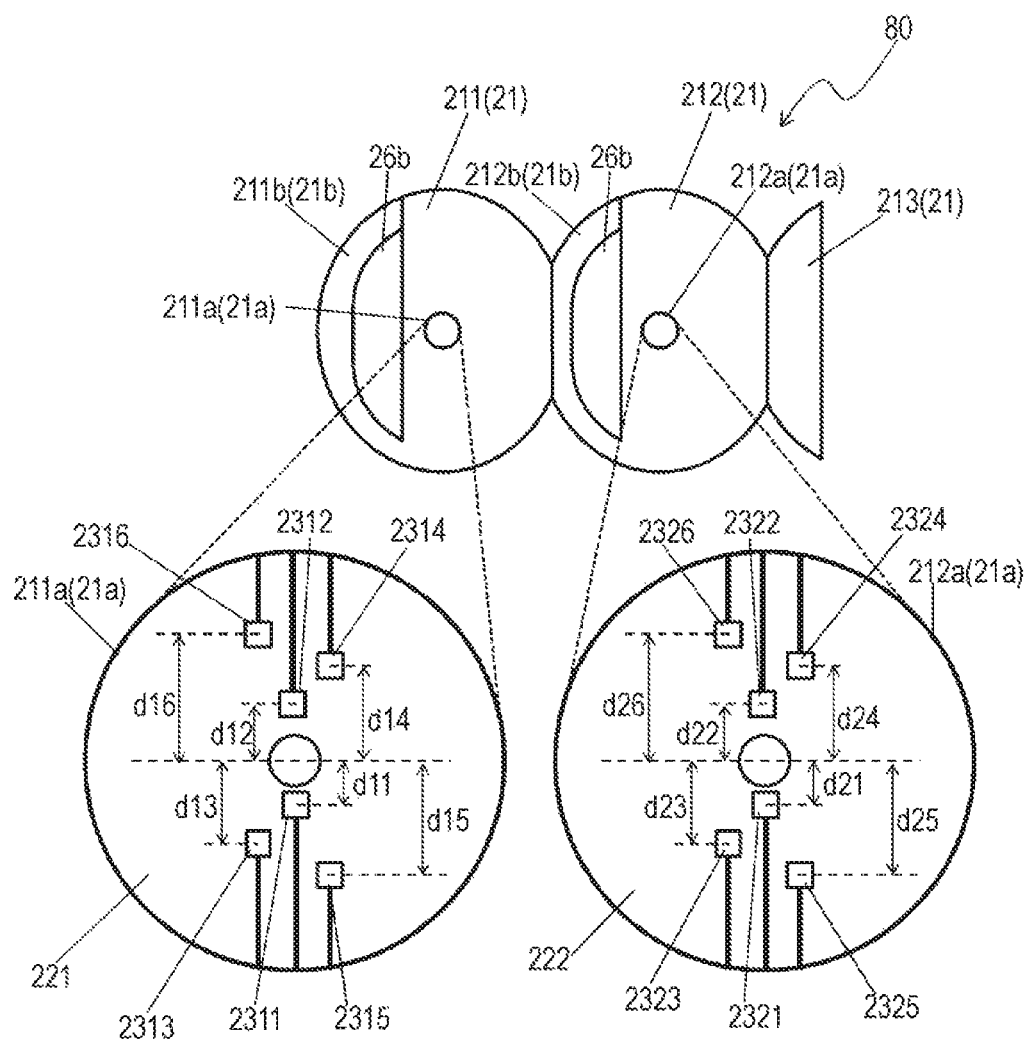
FIG. 9A is a top view of still another electrochemical measurement plate in accordance with the embodiment.
Figure 9B:
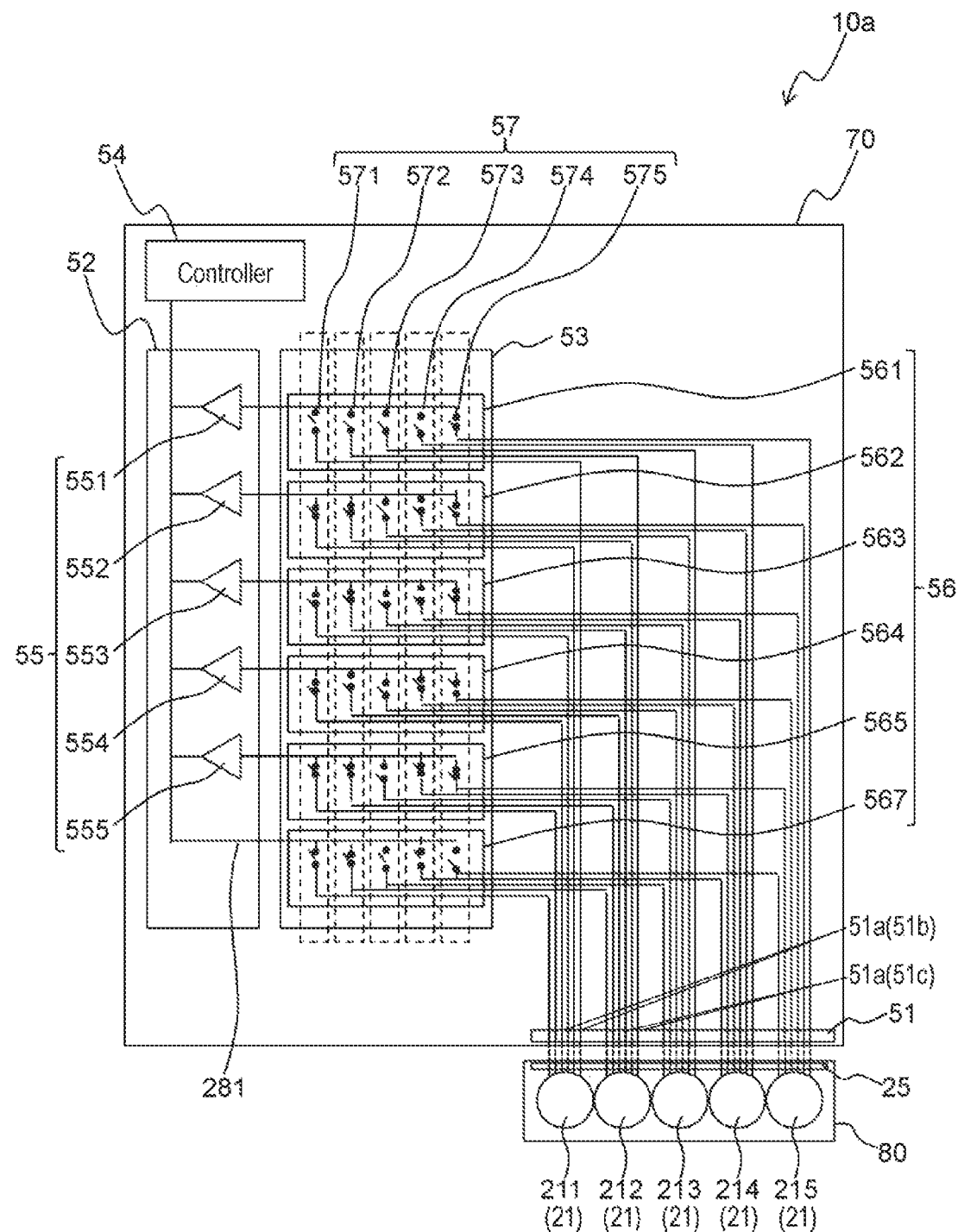
FIG. 9B is a circuit diagram of another electrochemical measurement device in accordance with the embodiment.

FIG. 9A is a top view of still another electrochemical measurement plate 80 in accordance with the embodiment. FIG. 9B is a circuit diagram of another electrochemical measurement system 10a in accordance with the embodiment, and mainly shows a circuit of electrochemical measurement device 70. In FIGS. 9A and 9B, components identical to those of electrochemical measurement system 10 shown in FIGS. 1 to 4 are denoted by the same reference numerals.

Electrochemical measurement plate 80 includes plural counter electrodes 26b provided within plural wells 21, respectively, instead of counter electrode 26 provided in well 24 of electrochemical measurement plate 20 shown in FIGS. 1 to 4. In the embodiment, each of counter electrodes 26b is provided on side wall surface 21b of each of wells 21. Plural counter electrodes 26b are provided around the mount portions in wells 21, respectively.

Switching section 53 of electrochemical measurement device 70 includes switching unit 567 including plural switching elements 57. Counter electrodes 26b provided in plural wells 21 are connected to plural switching elements 57 of switching unit 567 of switching section 53, respectively. Switching unit 567 switches counter electrodes 26b such that counter electrodes 26b provided within the same wells 21 as those including measurement electrodes 23 connected to measurement circuits 55 are connected to controller 54 at the same timing as the other switching units 561 to 565.

Figure 9C:
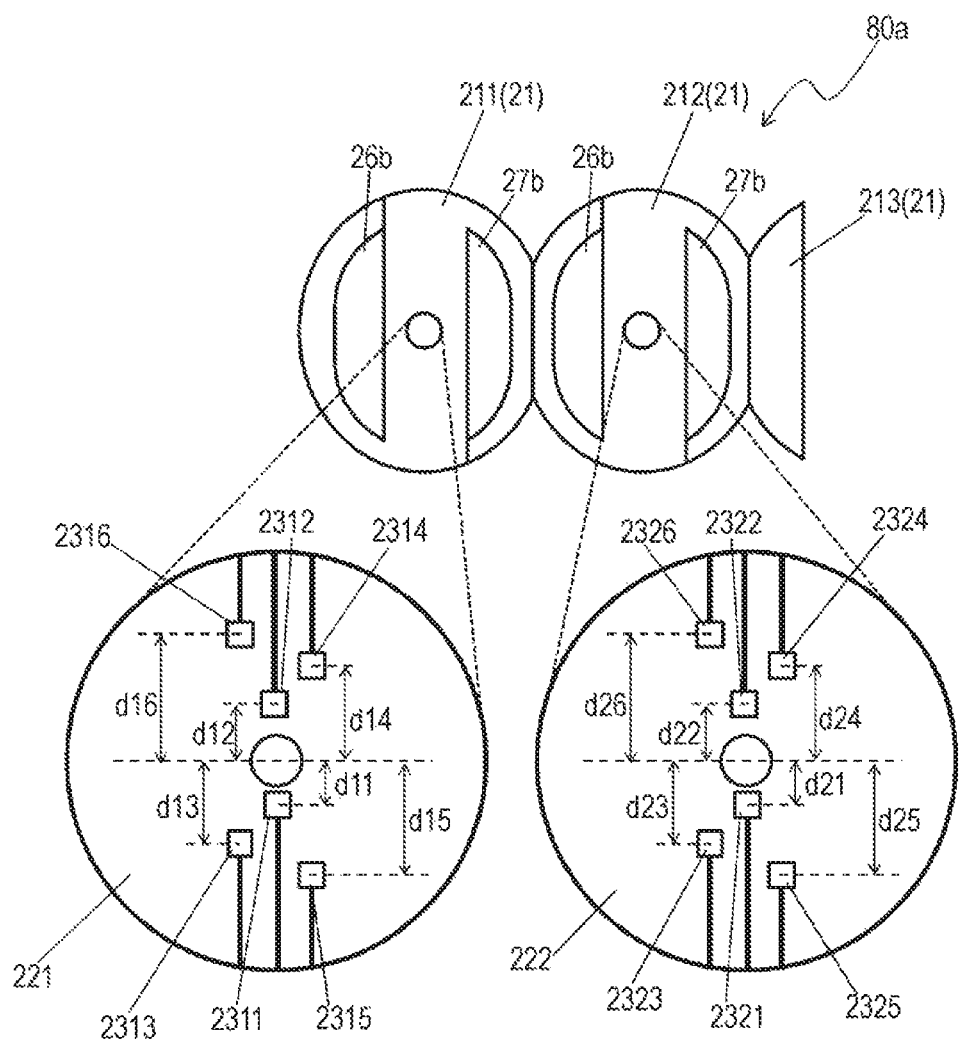
FIG. 9C is a top view of a further electrochemical measurement plate in accordance with the embodiment.

Counter electrodes 26b has a function of reference electrode 27 shown in FIG. 3A. A reference electrode separately from counter electrodes 26b may be provided. FIG. 9C is a top view of further electrochemical measurement plate 80a in accordance with the embodiment. In FIG. 9C, components identical to those of electrochemical measurement plate 80 shown in FIG. 9A are denoted by the same reference numerals. Electrochemical measurement plate 80a includes plural reference electrodes 27b provided within plural wells 21 of electrochemical measurement plate 80 shown in FIG. 9A, respectively. In accordance with the embodiment, each of reference electrodes 27b is provided on side wall surface 21b of respective one of wells 21. In this case, in electrochemical measurement device 50, switching section 53 further includes a switching unit including plural switching elements 97 that are connected to plural reference electrodes 27b provided in plural wells 21, respectively.

Electrode group 51b of electrochemical measurement device 70 further includes connector terminals 51a connected to counter electrodes 26b provided around mount portion 221. Electrode group 51c further includes connector terminals 51a connected to counter electrodes 26b provided around mount portion 222. Switching section 53 further includes switching unit 567 that connects controller 54 selectively to plural connector terminals 51a that are connected to plural counter electrodes 26b, respectively.

Modification 2

Modification 2 of the electrochemical measurement device according to the embodiment will be described below with reference to drawings.

Figure 10:
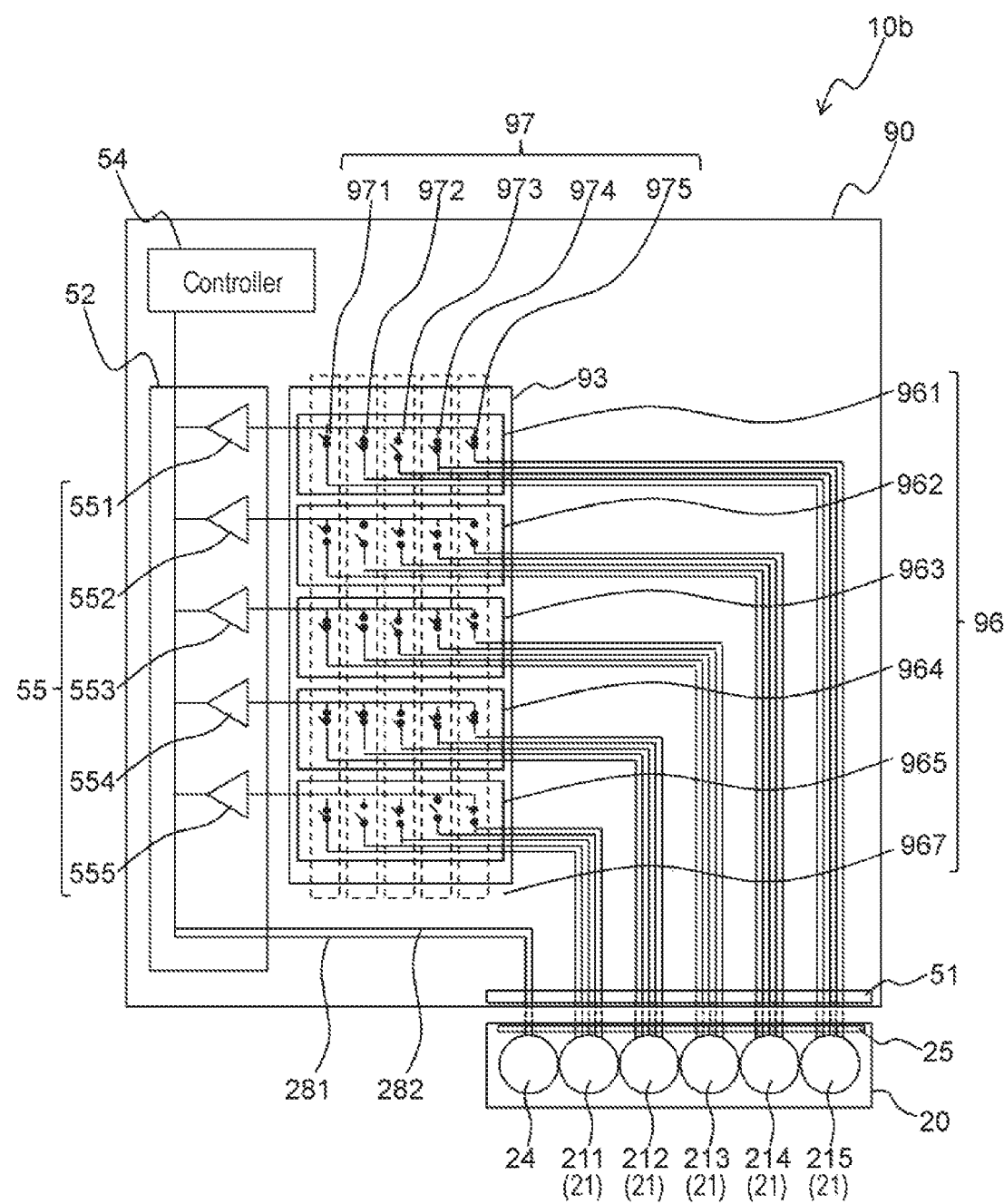
FIG. 10 is a circuit diagram of still another electrochemical measurement device in accordance with the embodiment.

FIG. 10 is a circuit diagram of another electrochemical measurement system 10b in accordance with the embodiment, and mainly shows a circuit of electrochemical measurement device 90. In FIG. 10, components identical to those of electrochemical measurement system 10 shown in FIGS. 1 to 4 are denoted by the same reference numerals.

Electrochemical measurement device 90 includes switching section 93 instead of switching section 53 of electrochemical measurement device 50 shown in FIG. 4. Switching section 93 includes switching units 96 the number of which corresponding to the number of plural wells 21 of electrochemical measurement plate 20. Each of switching units 96 is connected to plural measurement electrodes 23 provided within respective one of wells 21. In other words, each of switching units 96 includes the same number of switching elements 97 as measurement electrodes 23 provided within each well 21.

In electrochemical measurement plate 20 shown in FIG. 10, five measurement electrodes 23 are provided within each of wells 21 around mount portion 22. For example, well 211 includes five measurement electrodes 2311, 2312, 2313, 2314, and 2315. Electrochemical measurement device 90 includes five measurement circuits 55, five switching units 96, and five switching elements 97.

Each of measurement circuits 55 is connected to respective one of switching units 96.

In switching section 93 shown in FIG. 10, switching unit 961 includes switching elements 971, 972, 973, 974, and 975. Switching unit 961 is connected to measurement electrode 2311. Switching unit 962 is connected to measurement electrode 2312. Switching unit 963 is connected to measurement electrode 2313. Switching unit 964 is connected to measurement electrode 2314. Switching unit 965 is connected to measurement electrode 2315.

In switching unit 93, five switching elements 97 surrounded by a box of dashed lines are connected to measurement electrodes 23 located at an equal distance from mount portion 22 in each of wells 21. Controller 54 controls switching section 93 such that each of the five switching elements surrounded by each box of dashed lines shown in FIG. 10 are turned on and off simultaneously. Switching section 93 turns on and off switching elements 97 surrounded by a box of dashed lines as one group, and switches on and off the switching elements group by group.

This configuration allows electrochemical measurement device 90 to carry out electrochemical measurement for measurement electrodes 23 that are located at an equal distance from biological samples in different wells 21 at the same time. As a result, electrochemical measurement device 90 can accurately measure an electrochemical change dependent on distance.

Electrochemical measurement systems 10, 10a, and 10b, electrochemical measurement devices 50 and 90, and electrochemical measurement method in accordance with the embodiment are described with reference to measurement of respiratory activity of embryos, but this is merely illustrative. For example, they are widely applicable to testing and analysis of biological samples and the like, such as pharmacological tests on drug candidate compounds using model cells.

Furthermore, in measuring current values, the potential to be applied to measurement electrodes is not limited to the potential with a pulse waveform. For example, the electrochemical measurement for each well may be conducted by operating the switching section in a state in which a measurement potential with a constant value is applied to the measurement electrodes.

The controller does not necessarily control the switching of switching unit 56 that is connected to measurement electrodes 23 of well 21 in which no biological sample is introduced.

Although electrochemical measurement systems according to one or a plurality of aspects of the present disclosure have been described hereinabove based on the foregoing exemplary embodiments, the present disclosure is not limited to these exemplary embodiments. Various embodiments obtained by various modifications made to the exemplary embodiments that are conceivable by those skilled in the art, and various embodiments constructed by any combination of the constituent elements and features of the exemplary embodiments are also to be included within the scope of one or a plurality of aspects of the present disclosure, unless they depart from the spirit of the present disclosure.

INDUSTRIAL APPLICABILITY

An electrochemical measurement system is useful in, for example, electrochemical measurement of biological samples, such as embryos.

REFERENCE MARKS IN THE DRAWINGS 10 electrochemical measurement system
20, 80 electrochemical measurement plate
21, 24 well 22 mount portion
23 measurement electrode
25 outlet electrode portion
26, 26a, 26b counter electrode
27, 27a, 27b reference electrode
28 wiring
29 reservoir
50, 70, 90 electrochemical measurement plate
51 connector
51a connector terminal
51b, 51c electrode group
52 measurement unit
53, 93 switching section
54 controller
55 measurement circuit
56, 96 switching unit
57, 97 switching element
1001 measurement solution
102 biological sample
1021 biological sample (first biological sample)
1022 biological sample (second biological sample)

The invention claimed is:
1. An electrochemical measurement system comprising:
an electrochemical measurement plate configured to have a first biological sample and a second biological sample placed thereon; and
an electrochemical measurement device connected to the electrochemical measurement plate,
wherein the electrochemical measurement plate includes:
  a first well including a first mount portion configured to have the first biological sample placed thereon;
  a first measurement electrode group including an N number of first measurement electrodes provided within the first well around the first mount portion, where N is an integer greater than or equal to two;
  a second well including a second mount portion configured to have the second biological sample placed thereon; and
  a second measurement electrode group including an N number of second measurement electrodes provided within the second well around the second mount portion, and
wherein the electrochemical measurement device includes:
  an N number of measurement circuits;
  a switching section that connects the N number of measurement circuits selectively to the first measurement electrode group and the second measurement electrode group; and
  a controller that controls a potential applied to the N number of first measurement electrodes and a potential applied to the N number of second measurement electrodes,
wherein a first distance between the first mount portion and a certain first measurement electrode out of the N number of first measurement electrodes is less than a second distance between the first mount portion and a further first measurement electrode out of the N number of first measurement electrodes,
wherein a third distance between the second mount portion and a certain second measurement electrode out of the N number of second measurement electrodes is less than a fourth distance between the second mount portion and a further second measurement electrode out of the N number of second measurement electrodes,
wherein the first distance is equal to the third distance; and
wherein the second distance is equal to the fourth distance; and
wherein the switching section includes:
  a first switching unit that connects a first measurement circuit out of the N number of measurement circuits selectively to the certain first measurement electrode and the certain second measurement electrode; and
  a second switching unit that connects a second measurement circuit out of the N number of measurement circuits selectively to the further first measurement electrode and the further second measurement electrode,
wherein the electrochemical measurement plate further includes a counter electrode, and
wherein the electrochemical measurement device further includes a wiring connected between the counter electrode and the controller, the wiring not being connected to the switching section.
2. An electrochemical measurement device configured to be used with an electrochemical measurement plate having a first biological sa p e and a second biological sample placed thereon, the electrochemical measurement device comprising:
a first electrode group including an N number of first connector terminals, where N is an integer greater than or equal to 2;
a second electrode group including an N number of second connector terminals;
an N number of measurement circuits;
a switching section that connects the N number of measurement circuits selectively to the first electrode group and the second electrode group;
a third connector terminal;
a wiring connected to the third connector terminal; and
a controller,
wherein the electrochemical measurement plate includes:
  a first mount portion having the first biological sample placed thereon;
  an N number of first measurement electrodes provided within the first well around the first mount portion;
  a second mount portion having the second biological sample placed thereon; and
  an N number of second measurement electrodes provided within the second well around the second mount portion, and
wherein the N number of first connector terminals are configured to be connected to the N number of first measurement electrodes, respectively,
wherein the N number of second connector terminals are configured to be connected to the N number of second measurement electrodes, respectively, and
wherein the controller is configured to control a potential applied to the N number of first measurement electrodes and a potential applied to the N number of second measurement electrodes,
wherein a first distance between the first mount portion and a certain first measurement electrode out of the N number of first measurement electrodes is less than a second distance between the first mount portion and a further first measurement electrode out of the N number of first measurement electrodes,
wherein a third distance between the second mount portion and a certain second measurement electrode out of the N number of second measurement electrodes is less than a fourth distance between the second mount portion and the further second measurement electrode out of the N number of second measurement electrodes, wherein the first distance is equal to the third distance, and
wherein the second distance is equal to the fourth distance; and
wherein the switching section includes:
- a first switching unit that connects a first measurement circuit out of the N number of measurement circuits selectively to the certain first measurement electrode and the certain second measurement electrode; and
- a second switching, unit that connects a second measurement circuit out of the N number of measurement circuits selectively to the further first measurement electrode and the further second measurement electrode, wherein the wiring connects the third connector terminal to the controller, the wiring not being connected to the switching section, and
wherein the electrochemical measurement plate further includes a counter electrode that is connected to the third connector terminal.

3. An electrochemical measurement method comprising:
providing an electrochemical measurement plate which includes:
- a first well including a first mount portion;
- a first measurement electrode group including an N number of first measurement electrodes provided within the first well around the first mount portion, where N is an integer greater than or equal to two;
- a second well including a second mount portion;
- a second measurement electrode group including an N number of second measurement electrodes provided within the second well around the second mount portion; and
- a counter electrode;

providing an electrochemical measurement device including an N number of measurement circuits;
placing a first biological sample, a second biological sample, and a measurement solution in the electrochemical measurement plate such that the first biological sample is placed on the first mount portion, the second biological sample is placed on the second mount portion, and the measurement solution contacts the counter electrode, the first measurement electrode group, and the second measurement electrode group;

measuring current values in the N number of first measurement electrodes by applying a measurement potential to the counter electrode while the N number of measurement circuits are connected to the N number of first measurement electrodes;

after said measuring the current values in the N number of first measurement electrodes, switching the N number of measurement circuits so as to disconnect the N number of measurement circuits from the first measurement electrode group and connect the N number of measurement circuits to the second measurement electrode group; and measuring current values in the N number of second measurement electrodes by applying the measurement potential to the counter electrode while the N number of measurement circuits are connected to the N number of second measurement electrodes, and wherein said switching the N number of measurement circuits to disconnect the N number of measurement circuits from the first measurement electrode group and connect the N number of measurement circuits to the second measurement electrode group comprises, after said measuring the current values in the N number of first measurement electrodes, switching the N number of measurement circuits to disconnect the N number of measurement circuits from the first measurement electrode group and connect the N number of measurement circuits to the second measurement electrode group while a non-measurement potential is applied to the counter electrode.

4. The electrochemical measurement method according to claim 3, wherein the non-measurement potential is determined such that a current flows through none of the N number of first measurement electrodes and the N number of second measurement electrodes.

* * * * *